United States Patent
Yang et al.

(10) Patent No.: US 8,226,963 B2
(45) Date of Patent: Jul. 24, 2012

(54) FEED-THROUGH LIGNIN-PESTICIDE COMPOSITIONS

(75) Inventors: Kim W. Yang, Dallas, TX (US); Dennis Lee Murphy, Flower Mound, TX (US); Casey Shane White, Lewisville, TX (US); Maria N. Parfenova, Lewisville, TX (US); Joe Doyle McDaniel, Carrollton, TX (US); Jinren Ko, Bedford, TX (US)

(73) Assignee: Wellmark International, Schaumburg, IL (US)

( * ) Notice: Subject to any disclaimer, the term of this patent is extended or adjusted under 35 U.S.C. 154(b) by 445 days.

(21) Appl. No.: 11/535,450

(22) Filed: Sep. 26, 2006

(65) Prior Publication Data

US 2008/0113920 A1     May 15, 2008

Related U.S. Application Data

(60) Provisional application No. 60/722,513, filed on Sep. 30, 2005.

(51) Int. Cl.
*A01N 25/10* (2006.01)
*A01N 49/00* (2006.01)
*A01N 47/34* (2006.01)
*A01P 7/04* (2006.01)

(52) U.S. Cl. .......... 424/405; 514/22; 514/549; 514/552; 514/596

(58) Field of Classification Search ............... 514/22, 514/549, 552, 596; 424/405
See application file for complete search history.

(56) References Cited

U.S. PATENT DOCUMENTS

| | | | |
|---|---|---|---|
| 3,830,914 A | 8/1974 | Miller et al. | |
| 3,929,453 A | 12/1975 | Dimitri et al. | |
| 4,089,975 A | 5/1978 | Wade et al. | |
| 4,166,107 A * | 8/1979 | Miller et al. | 424/405 |
| 4,244,729 A * | 1/1981 | DelliColli et al. | 504/366 |
| 4,554,155 A | 11/1985 | Allan et al. | |
| 6,884,756 B2 | 4/2005 | Lynch et al. | |
| 7,771,749 B2 | 8/2010 | Asrar et al. | |
| 2004/0024026 A1 | 2/2004 | Morita et al. | |

FOREIGN PATENT DOCUMENTS

| | | |
|---|---|---|
| GB | 1511834 | 5/1978 |
| WO | WO 98/27830 | 7/1998 |
| WO | WO 00/42845 | 7/2000 |
| WO | WO 03/005816 A1 | 1/2003 |

OTHER PUBLICATIONS

Methoprene Pesticide Fact Sheet (EPA, Jun. 2001, pp. 1-9).*
Fernandez-Perez, Controlled Release of Imidacloprid from a Lignin Matrix: Water Release Kinetics and Soil Mobility Study; *J. Agric. Food Chem.*; 1998, 46, 3828-3834.

* cited by examiner

*Primary Examiner* — Kortney L Klinkel
(74) *Attorney, Agent, or Firm* — Kilpatrick Townsend & Stockton LLP

(57) ABSTRACT

The present invention provides lignin-pesticide complexes, methods for making lignin-pesticide complexes, and methods for treating or controlling insect infestations on animals by administering such complexes. Advantageously, the lignin-pesticide complexes of the present invention can be used in feed-through products to control insect infestation on livestock or pets. Various insects such as face flies, house flies, stable flies, and horn flies can be controlled and treated using the feed-through products of the present invention.

20 Claims, 7 Drawing Sheets

FEED-THROUGH LIGNIN-PESTICIDE COMPOSITIONS

CROSS-REFERENCE TO RELATED APPLICATIONS

The present application claims priority to U.S. Provisional Patent Application Ser. No. 60/722,513, filed Sep. 30, 2005, the teachings of which are hereby incorporated by reference in their entirety for all purposes.

BACKGROUND OF THE INVENTION

Scientists estimate that horn flies (*Haematobia irritans*) cost U.S. cattle producers at least $876 million each year. Together with fire ants and nuisance flies, they have a tremendously negative impact on the profits of farmers and ranchers in every industry.

Infestation occurs rapidly with 1000-4000 flies per animal in an untreated herd. In general, horn flies congregate on the back and shoulders of cattle and tend to rest quietly on the host. Horn flies rarely leave their host, except to lay eggs, change host animals, or remain outdoors when the host moves indoors.

Because they are a nuisance to the cattle, horn flies interrupt grazing patterns. The cattle tend to waste energy and even go off their feed. Due to horn fly infestations, calves are lighter at weaning by about 10-25 pounds. In addition, a 14% weight loss over a 120 day fly period can amount to 26 lbs. per head. In the summer season, horn flies can cause a loss of about 15-50 lbs. per head. At $0.90 per lb., a 30 lb. weight loss equals a $27.00 loss per head. Moreover, cows can go out of condition during breeding.

In addition, flies such as stable flies (*Stomoxys calcitrans*), house flies (*Musca domestica*), and face flies (*Musca autumnalis*) have a tremendously negative impact on animal health and economics. Stable flies are blood and flesh eaters with a strong painful bite that tend to reproduce in drier manure and straw combination environments. Their bite is so irritating that animals such as cattle do not feed, thereby causing a significant loss in their weight gain and a loss in profits of over $1 billion each year. House flies typically breed in manure, rotting material, or other moist places. Although house flies do not feed directly on animals, they annoy workers and reduce worker efficiency. Since house flies associate with manure and tend to enter homes, they are an efficient vector of disease and cause public health concerns. In fact, house flies are capable of transmitting numerous pathogens such as *E. coli, Salmonella*, and dysentery. Face flies are true manure breeders and cause pink eye and reduced weight gain in animals infested with them. The cost of face fly infestations, which include treating pink eye with antibiotics, amounts to over $150 million each year.

U.S. Pat. No. 3,929,453 discloses composites of lignin and biological active materials. The biologically active agent is either entrapped by the lignin macromolecular matrix or held by physical-chemical forces of van der Waal's, hydrogen bonding or ion association types. The active agent is slowly released on application either by diffusion through the lignin solid, or through degradation or dissolution of the lignin.

In view of the foregoing, there is a need in the art for more effective pesticide formulations that are economical and have low side-effects. There is also a need in the art for methods to control and treat insect infestations on livestock (e.g., horn fly, stable fly, house fly, or face fly infestations on cattle) and pets using such pesticide formulations. The present invention satisfies these and other needs.

BRIEF SUMMARY OF THE INVENTION

The present invention provides lignin-pesticide complexes, methods for making lignin-pesticide complexes, and methods for treating, controlling, preventing, and/or reducing insect infestations on animals by administering such complexes. Advantageously, in preferred embodiments, the lignin-pesticide complexes of the present invention can be formulated as feed-through products to control insect infestation on livestock and pets. Various insects can be controlled and treated using the feed-through products of the present invention. As a non-limiting example, horn flies are especially susceptible to the inventive feed-through products.

As such, in one aspect, the present invention provides a lignin-pesticide complex, the complex comprising:
(a) a lignin; and
(b) a pesticide, wherein the lignin and the pesticide are associated as a complex.

In one preferred aspect, the lignin-pesticide complex is formulated as a feed-through animal product.

In another aspect, the present invention provides a method for controlling a manure breeding insect on an animal, the method comprising:
(a) administering a lignin-pesticide complex as a feed-through product to the animal; and
(b) allowing the feed-through product to pass through the animal intact into an excrement, wherein the pesticide is subsequently bioavailable in the manure, thereby controlling the manure breeding insect.

In yet another aspect, the present invention provides a method for making a lignin-pesticide complex, the method comprising:
(a) spraying a pesticide onto a lignin to form a lignin-pesticide mixture; and
(b) aging the lignin-pesticide mixture for about one to about two years at room temperature.

In still yet another aspect, the present invention provides a method for making a lignin-pesticide complex, the method comprising:
(a) dissolving a pesticide in an organic solvent to form a pesticide solution;
(b) spraying the pesticide solution onto a lignin; and
(c) vaporizing the organic solvent.

In a further aspect, the present invention provides a method for making a lignin-pesticide complex, the method comprising:
(a) dissolving a pesticide in a water miscible organic solvent (such as a lower alkanol or alkanone), or alternatively, forming an oil in water emulsion or microemulsion of the pesticide to form a pesticide solution;
(b) dispersing a lignin in water to form a lignin suspension; and
(c) adding the pesticide solution to the lignin suspension or adding the pesticide O/W emulsion or microemulsion to the lignin suspension to form the lignin-pesticide complex.

In a preferred embodiment, the emulsion or microemulsion system in step (c) is destroyed (or de-emulsified, such as adding electrolytes) to force the pesticide out of the emulsion.

In another aspect, the present invention provides a method for making a lignin-pesticide complex, the method comprising:
(a) vaporizing a pesticide under vacuum and heat to form a pesticide vapor; and
(b) mixing the pesticide vapor with a lignin.

In yet another aspect, the present invention provides a method for making a lignin-pesticide complex, the method comprising:

(a) spraying a pesticide onto a lignin to form a lignin-pesticide mixture; and (b) placing the lignin-pesticide mixture under nitrogen or vacuum; and (c) heating the lignin-pesticide mixture to an elevated temperature.

Other objects, features, and advantages of the present invention will be apparent to one of skill in the art from the following detailed description and figures.

DETAILED DESCRIPTION OF THE INVENTION

I. General Overview

Figure 1:
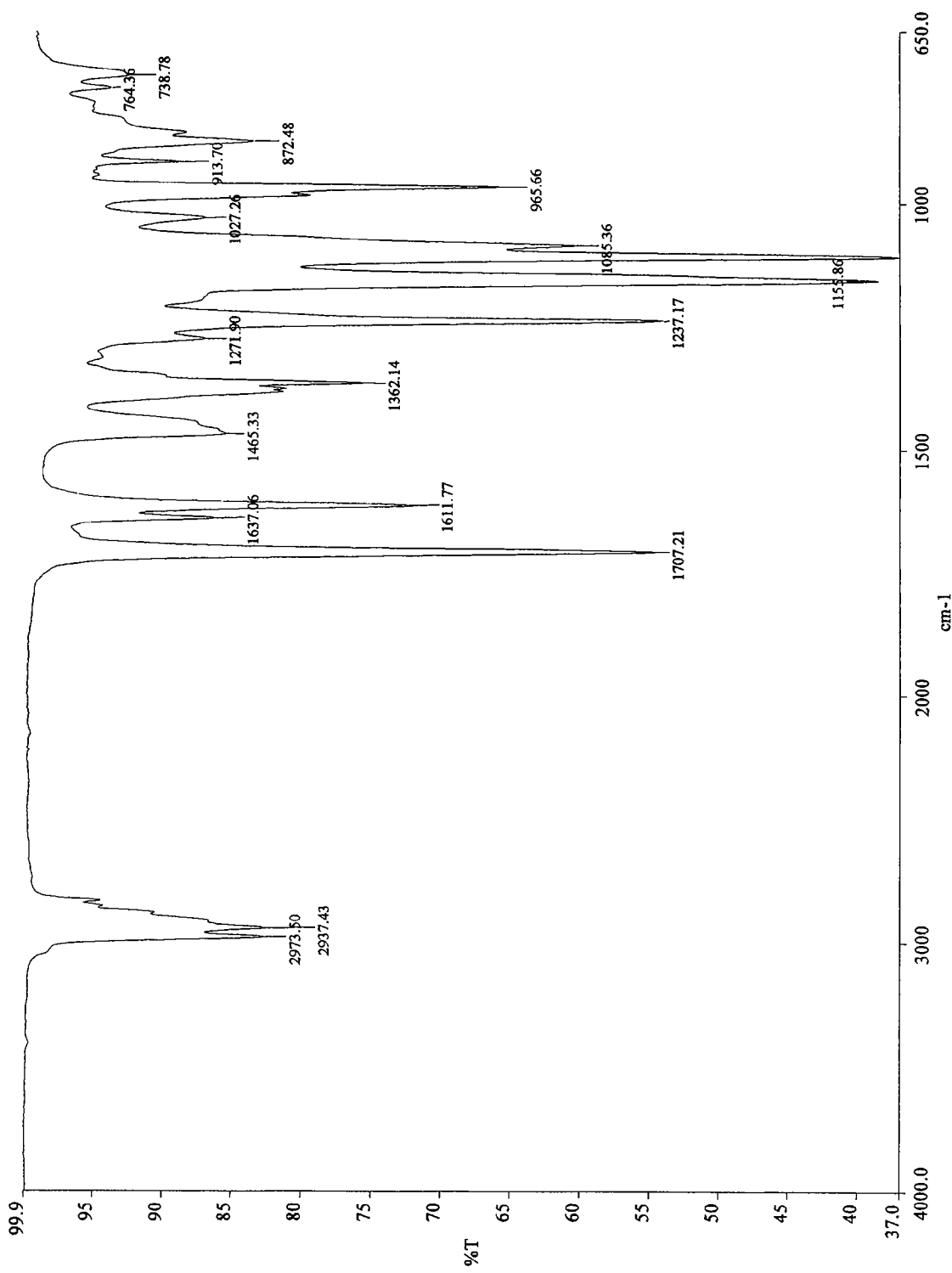
FIG. 1 shows the Fourier Transform Infrared (FTIR) spectrum of a methoprene standard.

The present invention provides lignin-pesticide complexes, methods for making lignin-pesticide complexes, and methods for treating, controlling, preventing, and/or reducing insect infestations in animals by administering such complexes. Advantageously, in preferred embodiments, the lignin-pesticide complexes of the present invention can be used in feed-through products to control insect infestation on livestock (e.g., cattle (bovine), sheep, swine, goats, poultry, horses (equine), fur-bearing animals and pets (e.g., cats, dogs, etc.). Various insects can be controlled and treated using the feed-through products of the present invention. These include, but are not limited to, manure breeding insects such as face flies, house flies, stable flies, and horn flies. Horn flies are especially susceptible to the feed-through products of the present invention.

The present invention is based upon the surprising discovery that only formulations containing a lignin-pesticide complex are suitable as efficient and safe feed-through animal products. In contrast, formulations that rely on enteric coated pesticides, pesticides encapsulated in a polymeric matrix, or pesticides impregnated in charcoal or silica require very high doses as feed-through animal products. Due to the presence of an intermolecular interaction (e.g., hydrogen bond) between the lignin and the pesticide, the lignin-pesticide complexes of the present invention advantageously protect pesticides such as methoprene against intestinal absorption and enzyme and microbial digestion in an animal and allow the pesticide to pass through the animal into its manure, where it is released and bioavailable for effective pest control. As a result, the present invention provides solutions to two problems relating to the control of pests in livestock and pets: (1) the side-effects (e.g., toxicity) associated with feed-through products are prevented, reduced, and/or eliminated because the lignin-pesticide complexes are resistant to destruction in the stomach and intestinal absorption; and (2) lower doses of pesticide can be used in feed-through products because substantially more pesticide is found in the manure, thereby creating an economical means for using expensive pesticides.

II. Description of the Embodiments

In one aspect, the present invention provides a lignin-pesticide complex formulated as a feed-through animal product, the complex comprising:

(a) a lignin; and (b) a pesticide, wherein the lignin and the pesticide are associated as a complex.

In one embodiment, the lignin is an alkali lignin, a lignosulphonate (sulfite lignin), an oxylignin; a chlorolignin; a protolignin; a lignin liquor; salts thereof; derivatives thereof; or combinations thereof. Preferably, the lignin is an alkali lignin such as a Kraft lignin, a sodium salt, a potassium salt, an ammonia salt, an amine salt (e.g., trimethylamine) of lignin, or a soda lignin.

In certain instances, the pesticide is chemically bonded with lignin. In certain other instances, the lignin is associated with the pesticide through hydrogen bonding or other intermolecular forces. Examples of other intermolecular forces include, without limitation, ionic, van der Waals, and dipole-dipole interactions. Preferably, the lignin is associated with the pesticide through hydrogen bonding or van der Waals forces. One skilled in the art will appreciate that other covalent or non-covalent interactions between the lignin and pesticide are within the scope of the present invention.

In another embodiment, the pesticide is an insect growth regulator (IGR). Suitable IGRs for use in the present invention include, without limitation, chitin synthesis inhibitors, juvenile hormone mimics, juvenile hormones, molting hormone agonists, molting hormones, molting inhibitors, precocenes, unclassified insect growth regulators, and mixtures thereof. Preferred IGRs include, for example, methoprene, hydroprene, kinoprene, fenoxycarb, pyriproxifen, cyromazine, diflubenzuron, novaluron, and mixtures thereof. In a particularly preferred embodiment, the IGR is methoprene. Additional IGRs that are suitable for use in the lignin-pesticide complexes of the present invention are described below.

In yet another embodiment, the pesticide is an adulticide. Suitable adulticides for use in the present invention include, but are not limited to, organophosphates, carbamates, pyrethroids, neonicotinoid insecticides, spinosyn, and the like. In certain instances, the adulticide is an organophosphate such as tetrachlorvinphos. In certain other instances, the adulticide is a neonicotinoid insecticide such as imidacloprid, acetamiprid, nithiazine, or thiomethoxam. Additional adulticides that are suitable for use in the lignin-pesticide complexes of the present invention are described below.

In another aspect, the present invention provides a method for controlling a manure breeding insect on an animal, the method comprising:

(a) administering a lignin-pesticide complex as a feed-through product to the animal; and (b) allowing the feed-through product to pass through the animal intact into an excrement, wherein the pesticide is subsequently bioavailable in the manure, thereby controlling the manure breeding insect.

In certain instances, the animal is livestock. Examples of livestock that can be administered the feed-through products of the present invention include, without limitation, cattle, sheep, swine, goats, poultry (e.g., chickens, turkeys, etc.), horses, and fur-bearing animals. Non-limiting examples of fur-bearing animals that can be administered the feed-through products of the present invention include rabbits, foxes, minks, chinchillas, beavers, muskrats, martens, otters, ferrets, nutrias, and bears. In certain other instances, the animal is a pet. Examples of pets that can be administered the feed-through products of the present invention include, but are not limited to, cats, dogs, rabbits, birds, horses, rodents, reptiles and the like.

In one embodiment, the pesticide is an insect growth regulator (IGR). Suitable IGRs for use in the present invention include, without limitation, chitin synthesis inhibitors, juvenile hormone mimics, juvenile hormones, molting hormone agonists, molting hormones, molting inhibitors, precocenes, unclassified insect growth regulators, and mixtures thereof. Preferred IGRs include, for example, methoprene, hydroprene, kinoprene, fenoxycarb, pyriproxifen, cyromazine, diflubenzuron, novaluron, and mixtures thereof. In a particularly preferred embodiment, the IGR is methoprene. Additional IGRs that are suitable for use in the lignin-pesticide formulations of the present invention are described below.

In another embodiment, the pesticide is an adulticide. Suitable adulticides for use in the present invention include, but are not limited to, organophosphates, carbamates, pyrethroids, neonicotinoid insecticides, spinosyn, and the like. In certain instances, the adulticide is an organophosphate such as tetrachlorvinphos. In certain other instances, the adulticide is a neonicotinoid insecticide such as imidacloprid, acetamiprid, nithiazine, or thiomethoxam. Additional adulticides that are suitable for use in the lignin-pesticide formulations of the present invention are described below.

In yet another aspect, the present invention provides a method for making a lignin-pesticide complex, the method comprising:
(a) spraying a pesticide onto a lignin to form a lignin-pesticide mixture; and
(b) aging the lignin-pesticide mixture for about one to about two years at room temperature.

In one embodiment, methoprene is sprayed onto lignin powder in a mixer and the resulting mixture is allowed to age for about one to two years at room temperature. In certain instances, lignin-methoprene complex formation is accelerated by storing the mixture under elevated temperature (e.g., about 40° C. to 50° C.).

In still yet another aspect, the present invention provides a method for making a lignin-pesticide complex, the method comprising:
(a) dissolving a pesticide in an organic solvent to form a pesticide solution;
(b) spraying the pesticide solution onto a lignin; and
(c) vaporizing the organic solvent.

In one embodiment, methoprene, tetrachlorvinphos, or cyromazine is dissolved in an organic solvent such as an alcohol (e.g., methanol, ethanol, isopropanol), ketone (e.g., acetone, methylethylketone), ester (e.g., methyl acetate, ethyl acetate, amyl acetate), acetonitrile, aromatic hydrocarbon, or aliphatic hydrocarbon. The solution is then sprayed onto lignin powder in a mixer. Finally, the solvent is vaporized to obtain the lignin-pesticide complex.

In a further aspect, the present invention provides a method for making a lignin-pesticide complex, the method comprising:
(a) dissolving a pesticide in a water-miscible alcohol to form a pesticide solution;
(b) dispersing a lignin in water to form a lignin suspension; and
(c) adding the pesticide solution to the lignin suspension.

In one embodiment, methoprene is dissolved in a water-miscible alcohol (e.g., methanol, ethanol, isopropanol). While stirring, lignin is dispersed in water to form a lignin suspension. Next, the methoprene/alcohol solution is added drop-wise to the lignin suspension. A clear supernatant without an oily film floating on top of the water indicates that the pesticide has been deposited onto the fine lignin particles. Filtration and drying steps are then employed to obtain the lignin-methoprene complex as a powder.

In another aspect, the present invention provides a method for making a lignin-pesticide complex, the method comprising:
(a) vaporizing a pesticide under vacuum and heat to form a pesticide vapor; and
(b) mixing the pesticide vapor with a lignin.

In one embodiment, methoprene is vaporized under vacuum and heat. The resulting vapor is then introduced into a sealed vessel filled with powdered lignin. Agitation or rotation of the vessel assures the uniformity of the lignin-methoprene complex.

In yet another aspect, the present invention provides a method for making a lignin-pesticide complex, the method comprising:
(a) spraying a pesticide onto a lignin to form a lignin-pesticide mixture; and
(b) placing the lignin-pesticide mixture under nitrogen or vacuum; and
(c) heating the lignin-pesticide mixture to an elevated temperature.

In one embodiment, atomized methoprene is sprayed onto lignin. The mixture is then placed into a sealed vessel under nitrogen or vacuum and heated to an elevated temperature (e.g., up to 300° C.) for about 30 minutes to obtain the lignin-methoprene complex.

III. Pesticides

Various pesticides are suitable for use in the present invention. The term "pesticide" as employed herein is intended to include any active material used for the control of unwanted plants, animals, or microorganisms, such as mosquitoes, fungi, algae, snails, weeds, and the like. Suitable pesticides include, without limitation, insecticides, biocides, herbicides, fungicides, rodenticides, insect repellants, antimicrobials, and other materials utilizable in the environment to prevent, destroy, repel, and/or reduce pests.

In a preferred embodiment, the pesticide of the present invention is an insect growth regulator (IGR). Insect growth regulators, including juvenile hormones, are well known for their use and efficacy in controlling or eliminating insect infestation in humans, in animals, and in both residential and industrial environments. Many types of insects are controllable by insect growth regulators, including, without limitation, flies (e.g., face flies, house flies, stable flies, and horn flies), fleas, mosquitoes, flour beetles, cigarette beetles, and cockroaches.

The insect growth regulators vary widely in chemical composition, with two of the more prominent classes comprising 2,4-dienoic acids and phenoxyphenoxy compounds, e.g., phenoxyphenoxyalkoxyheterocyclics. Benzoylureas and triazine derivatives are also suitable for use in the present invention as insect growth regulators. Examples of 2,4-dienoic acids and related compounds include, without limitation, methoprene, hydroprene, neotenin, and epiphenonane. As used herein, "methoprene" includes R-methoprene, S-methoprene, and all mixtures of R- and S-methoprene. S-methoprene is the preferred methoprene. Examples of phenoxyphenoxy compounds include, without limitation, fenoxycarb and pyriproxyfen. Examples of benzoylureas include, without limitation, lufenuron, diflubenzuron, terflubenzuron, triflumaron, hexaflumaron, and flucycloxuron. An example of a triazine derivative is 2-cyclopropylamino-4,6-bis(dimethylamino)-s-triazine.

Suitable IGRs for use in the present invention include, without limitation, chitin synthesis inhibitors such as bistrifluron, buprofezin, chlorfluazuron, cyromazine, diflubenzuron, flucycloxuron, flufenoxuron, hexaflumuron, lufenuron, novaluron, noviflumuron, penfluron, teflubenzuron, and triflumuron; juvenile hormone mimics such as epofenonane, fenoxycarb, hydroprene, kinoprene, methoprene, pyriproxyfen, and triprene; juvenile hormones such as juvenile hormone I, juvenile hormone II, and juvenile hormone III; molting hormone agonists such as chromafenozide, halofenozide, methoxyfenozide, and tebufenozide; molting hormones such as α-ecdysone and ecdysterone; molting inhibitors such as diofenolan; precocenes such as precocene I, precocene II, and precocene III; unclassified insect growth regulators such as dicyclanil; other IGRs; and mixtures thereof. Preferred IGRs include, for example, methoprene, hydroprene, kinoprene, fenoxycarb, pyriproxifen, cyromazine, diflubenzuron, novaluron, and mixtures thereof. In a particularly preferred embodiment, the IGR is methoprene.

In another embodiment, the pesticide of the present invention is an adulticide. The term "adulticide" as used herein refers to a pesticide designed to kill adult insects. Suitable adulticides for use in the present invention include, for example, organophosphates, carbamates, pyrethroids, neonicotinoid insecticides, spinosyn, and the like. Examples of organophosphate compounds include, without limitation, acephate, azinphosmethyl, bensulide, cadusafos, chlorethoxyfos, chlorpyrifos, chlorpyrifos methyl, chlorthiophos, coumaphos, dialiflor, diazinon, dichlorvos, dicrotophos, dimethoate, dioxathion, disulfoton, ethion, ethoprop, ethyl parathion, fenamiphos, fenitrothion, fenthion, fonofos, isazophos methyl, isofenphos, malathion, methamidophos, methidathion, methyl parathion, mevinphos, monocrotophos, naled, oxydemeton methyl, phorate, phosalone, phosmet, phosphamidon, phostebupirim, pirimiphos methyl, profenofos, propetamphos, sulfotepp, sulprofos, temephos, terbufos, tetrachlorvinphos, tribufos, and trichlorfon. Preferably, the organophosphate pesticide is tetrachlorvinphos. Examples of carbamate compounds include, without limitation, aldicarb, bendiocarb, carbaryl, carbofuron, fenoxycarb, methomyl, pirimicarb, and propoxur. Non-limiting examples of pyrethroid compounds include allethrin, bifenthrin, bioresmethrin, cyfluthrin, cyhalothrin, cypermethrin, deltamethrin, esfenvalerate, fenvalerate, flumethrin, permethrin, pyrethrin, resmethrin, and their synergists (e.g., piperonyl butoxide). Examples of neonicotinoid insecticides include, without limitation, imidacloprid, acetamiprid, nithiazine, and thiomethoxam. One skilled in the art will know of additional adulticides suitable for use in the present invention.

In certain instances, the amount of pesticide in the complex is from about 0.001% w/w to about 99% w/w, e.g., from about 0.01% w/w to about 75% w/w, from about 0.01% w/w to about 50% w/w, from about 0.01% w/w to about 20% w/w, or from about 0.01% w/w to about 10% w/w. Preferably, the amount of pesticide in the complex is about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or 10% w/w.

IV. Lignins

Various lignins are suitable for use in the present invention. The term "lignin" as used herein refers to a complex polymeric compound found in woody plants, trees, and agricultural crops. Lignins are typically produced as a co-product of the paper industry, separated from trees by a chemical pulping process. However, one skilled in the art will appreciate that any plant source of lignin (e.g., hard wood lignin, soft wood lignin, grass lignin, straw lignin, and bamboo lignin), nut source of lignin (e.g., pecan shell, walnut shell, peanut shell, etc. as a fine powder), seed source of lignin (e.g., cotton seed shell as a fine powder), and the like can used to obtain lignins suitable for use in the present invention. For example, cosmetic grade very finely powdered pecan or walnut shells or cotton seed shells may contain significant amounts of lignin.

Examples of lignins that can be obtained from plants, trees, and/or agricultural crops include, without limitation, alkali lignins such as Kraft lignins (sulfate lignins), sodium or potassium salts of lignins, or soda lignins; lignosulphonates (sulfite lignins); oxylignins; chlorolignins; protolignins; lignin liquors; salts thereof; derivatives thereof; and combinations thereof. Lignins can be obtained from the Kraft pulping process and are generally not water-soluble. Sodium or potassium salts of lignins are generally water-soluble. Lignosulphonates are products of sulfite pulping and are typically hydrophilic. In preferred embodiments of the present invention, the lignin used in the lignin-pesticide complex is an alkali lignin such as a Kraft lignin, a sodium salt of lignin, a potassium salt of lignin, a soda lignin, or combinations thereof. Lignins obtained from various sources can also be chemically modified (e.g., etherified, esterified, alkylated, halogenated, nitrated, mercurated, hydrogenated) using methods known in the art. In certain instances, lignins can be used as a whole liquor or, in certain other instances, as a purified material (e.g., fine powder) wherein the saccharide and/or inorganic constituents have been partially or wholly removed.

In one embodiment, a preferred lignosulfonate is ammonium lignosulfonate (AL). As known in the art, ammonium lignosulfonate is a sulfonate salt, which is by-product of either the acid sulfite pulping process or the chemi(thermo)mechanical (CTMP) pulping. During the pulping process, the lignin in the wood chips (from either hardwood or softwood) is subjected to reaction with an aqueous bisulfite salt at elevated temperature and pressure, and is rendered water soluble by depolymerization and sulfonation reactions. Both reactions typically take place in the β-position in the propane side chain of the lignin molecule, and the resulting lignosulfonate molecule contains one sulfonate group per two phenylpropane units.

The typical weight average molecular weight of the ammonium lignosulfonate is about 30,000, and its number average molecular weight is about 3,000. The resulting lignosulfonate is dissolved in the spent sulfite pulping liquor along with a variety of carbohydrates that are formed by degradation of the hemicellulose components of the wood.

The AL can be provided as a powder, a dispersion, or a solution. Examples of AL solutions are LIGNOSITE® 1740 from Georgia-Pacific West, Inc., of Bellingham, Wash., NORLIG TSFL and NORLIG TSFL-4 from Borregaard LignoTech, Inc., of Rothschild, Wis., and Weschem AS from Wesco Technologies, Ltd., of San Clemente, Calif. The LIGNOSITE® 1740 solution contains 48% by weight total solids, more than 60% of which is AL solids. The Weschem AS dry solids contain more than 57% lignosulfonate and more than 24% reducing sugars by weight.

Other lignosulfonate powders, dispersions or solutions can be used in place of ammonium lignosulfonate. For example, calcium lignosulfonate (CaLS), zinc lignosulfonate (ZL), ferric lignosulfonate (FL), chromium lignosulfonate (CrL), magnesium lignosulfonate (MgL), sodium lignosulfonate (NaLS), copper lignosulfonate (CuLS), and manganese lignosulfonate (MnL) can be used. Examples of zinc lignosulfonate are: in solution form, Weschem Zn from Wesco Technologies, Ltd.; and in powder form, Zinc KE-MIN® micronutrient lignosulfonate from Georgia-Pacific West, Inc., and NORLIG®. Zn from Borregaard LignoTech, Inc. Mixtures of the various lignosulfonates can also be used.

In certain instances, the amount of lignin in the lignin-pesticide complex is from about 0.001% w/w to about 99% w/w, e.g., from about 0.01% w/w to about 75% w/w, from about 0.01% w/w to about 50% w/w, from about 0.01% w/w to about 20% w/w, or from about 0.01% w/w to about 10% w/w.

In certain instances, the ratio of lignin to pesticide is from about 1:1000 to about 1:1 w/w, e.g., from about 1:500 to about 1:100 w/w, from about 1:100 to about 1:50 w/w, from about 1:50 to about 1:25 w/w, from about 1:25 to about 1:10 w/w, or from about 1:10 to about 1:1 w/w (e.g., about 1:10, 1:9, 1:8, 1:7, 1:6, 1:5, 1:4, 1:3, 1:2, or 1:1 w/w, or fractional integers thereof). In certain other instances, the ratio of lignin to pesticide is from about 1000:1 to about 1:1 w/w, e.g., from about 500:1 to about 100:1 w/w, from about 100:1 to about 50:1 w/w, from about 50:1 to about 25:1 w/w, from about 25:1 to about 10:1 w/w, or from about 10:1 to about 1:1 w/w (e.g., about 10:1, 9:1, 8:1, 7:1, 6:1, 5:1, 4:1, 3:1, 2:1, or 1:1 w/w, or fractional integers thereof). As a non-limiting example, the ratio of lignin to methoprene is preferably from about 99:1 to about 49:1 w/w (e.g., about 98-99% lignin to about 1-2% methoprene). One skilled in the art will appreciate that optimum feed-through effects can be achieved by making adjustments within these ranges.

V. Formulations

The lignin-pesticide complexes of the present invention are preferably formulated into animal feed, feed mixtures, or feed supplements as feed-through products to animals. The formulations can be solid or liquid formulations and can take a final form such as a granule, a particle, a pellet, a capsule, a microcapsule, a cube, a tablet, a microtablet, a complete feed ration, a liquid feed ration, an emulsion concentrate, a solution, an oil-in-water emulsion, a wettable powder, a soluble powder, a suspension concentrate, a water-based liquid concentrate, an aerosol, a water-soluble granule, a dust, a water-dispersible granule, and a gel.

In some embodiments, the lignin-pesticide formulations of the present invention are solid formulations. Such solid formulations can be, for example, a granule, a particle, a pellet, a capsule (e.g., a microcapsule), a tablet, a whole feed ration, and combinations thereof. In certain instances, the solid formulation is about 50 µm to about 5 mm in size. Preferably, the size is about 0.2 mm to about 2 mm in size, e.g., about 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 mm. As a non-limiting example, the solid formulations are homogenous granules, filtered through wire mesh such as 16 mesh or 40 mesh. The amount of carrier (e.g., solid carrier such as gypsum) in the solid formulations of the present invention can range from about 0% w/w to about 90% w/w.

In other embodiments, the lignin-pesticide formulations of the present invention comprise liquid carriers such as molasses, vegetable oils, corn steep, liquid feed supplements, esters from fatty acids of vegetable oils such as methylated coconut or soybean oil ester, and water. Mixtures of different liquids are often suitable as feed supplements. The amount of liquid carrier in the formulations of the present invention can range from about 0% w/w to about 90% w/w.

The lignin-pesticide formulations of the present invention can also be formulated and transported in a concentrated form which is subsequently diluted by the user before application. The presence of small amounts of a carrier which is a surfactant facilitates this process of dilution. Thus, a carrier in the formulations according to the present invention can be a surfactant. For example, the formulations can contain at least two or more carriers, at least one of which is a surfactant.

In certain instances, the ratio of pesticide to carrier is from about 1:1000 to about 1:1 w/w, e.g., from about 1:500 to about 1:100 w/w, from about 1:100 to about 1:50 w/w, from about 1:50 to about 1:25 w/w, from about 1:25 to about 1:10 w/w, or from about 1:10 to about 1:1 w/w. One skilled in the art will appreciate that optimum feed-through effects can be achieved by making adjustments within these ranges.

In further embodiments, the lignin-pesticide formulations of the present invention comprise a biopolymer. Preferably, the biopolymer extends the shelf-life of the formulation. Suitable biopolymers for use in the present invention include carbohydrates (e.g., saccharides) such as, for example, oligosaccharides, polysaccharides, and mixtures thereof. Non-limiting examples of polysaccharides include a cyclodextrin, a starch, a carboxymethyl cellulose salt, an alginate, a methyl cellulose, an ethyl cellulose, a hydroxypropyl cellulose, sucrose, a starch glycolic acid salt, molasses, lactose, dextrin, acacia, agar, guar, locust bean, tragacanth, xanthan, and combinations thereof. In certain instances, the carbohydrate is a water-soluble saccharide. In certain other instances, the carbohydrate is molasses. Suitable types of molasses include, but are not limited to, beet sugar molasses, citrus molasses, hemicellulose extract, starch molasses, cane sugar molasses, and combinations thereof. One skill in the art will know of other types of molasses suitable for use in the present invention.

Surprisingly, the biopolymer imparts a "crushing" or "tensile" strength onto the formulations of the present invention. This advantageous property extends the shelf-life and thus prolongs the stability of the lignin-pesticide formulations described herein.

In certain instances, the ratio of pesticide to biopolymer is from about 1:1000 to about 1:1 w/w, e.g., from about 1:500 to about 1:100 w/w, from about 1:100 to about 1:50 w/w, from about 1:50 to about 1:25 w/w, from about 1:25 to about 1:10 w/w, or from about 1:10 to about 1:1 w/w. In certain other instances, the ratio of pesticide to biopolymer is from about 1000:1 to about 1:1 w/w, e.g., from about 500:1 to about 100:1 w/w, from about 100:1 to about 50:1 w/w, from about 50:1 to about 25:1 w/w, from about 25:1 to about 10:1 w/w, or from about 10:1 to about 1:1 w/w. One skilled in the art will appreciate that optimum feed-through effects can be achieved by making adjustments within these ranges.

In some embodiments, the lignin-pesticide formulations further comprise a binding agent. In other embodiments, the formulations of the present invention optionally further comprise a taste masking agent.

In additional embodiments, the lignin-pesticide formulations of the present invention further comprise an antioxidant. Suitable antioxidants include, but are not limited to, Vitamin E, Vitamin A palmitate, ethoxyquin, propyl gallate, butylated hydroxyanisole (BHA), butylated hydroxytoluene (BHT), and combinations thereof.

In certain instances, the lignin-pesticide formulations of the present invention have an antioxidant effect without additional antioxidants being present. Without being bound by any particular theory, it is believed that in certain embodiments, the phenolic groups in lignin have an antioxidant effect. These phenolic groups help stabilize the pesticide (e.g., methoprene) preventing it from being destroyed rapidly by oxygen in the air.

In further embodiments of the present invention, the biological activity of the pesticide can be increased by including an adjuvant in the formulation. An adjuvant is defined herein as a substance which can increase the biological activity of a pesticide but is not itself significantly biologically active. The adjuvant can either be included in the formulation as a co-formulant or carrier, or can be added to the formulation containing the pesticide.

In certain instances, the formulations of the present invention also contain other stability agents such as clays (e.g., kaolin), magnesium or aluminum silicates for extended physical stability of the feed product, as well as combinations of clays and gums.

In some embodiments, the present formulations can be manufactured into a final form designed to be admixed with liquid feeds and liquid feed supplements. Examples of suitable formulations for the lignin-pesticide complexes of the present invention include, without limitation, an emulsion concentrate, a solution, an oil-in-water emulsion, a wettable powder, a soluble powder, a suspension concentrate, a water-based liquid concentrate, an aerosol, a water-soluble granule, a dust, a water-dispersible granule, a tablet, a capsule, and a gel. These formulations can be manufactured by well-established procedures such as, for example, intensive mixing and/or milling of the lignin-pesticide complex with any of the above-described ingredients, e.g., carriers, surface active compounds (e.g., surfactants), biopolymers, antioxidants, binding agents, taste masking agents, fillers, solvents, additives, adjuvants, etc., as well as other ingredients known to one skilled in the art. Surprisingly, the formulations of the present invention, when admixed into a liquid feed or liquid feed supplement, has the characteristic of reducing or eliminating stratification of the lignin-pesticide complex in the liquid feed or liquid feed supplement. As a result, the liquid feed or liquid feed supplement having the lignin-pesticide formulation admixed therein is usable for a longer period of time.

Various hydrophobic agents are suitable for use in the formulations of the present invention. In one embodiment, the hydrophobic agent is a hydrophobic solvent such as a fat, vegetable oil, mineral oil, or a combination thereof. The fat or vegetable oil can be, for example, a mono-glyceride, a di-glyceride, a tri-glyceride, or a mixture thereof. The mineral oil can be, for example, an aliphatic oil, a paraffinic oil, an isoparaffinic oil, or a mixture thereof. In certain instances, the ratio of pesticide to hydrophobic agent is from about 1:1000 to about 1:1 w/w, e.g., from about 1:500 to about 1:100 w/w, from about 1:100 to about 1:50 w/w, from about 1:50 to about 1:25 w/w, from about 1:25 to about 1:10 w/w, or from about 1:10 to about 1:1 w/w. In certain other instances, the ratio of pesticide to hydrophobic agent is from about 1000:1 to about 1:1 w/w, e.g., from about 500:1 to about 100:1 w/w, from about 100:1 to about 50:1 w/w, from about 50:1 to about 25:1 w/w, from about 25:1 to about 10:1 w/w, or from about 10:1 to about 1:1 w/w. One skilled in the art will appreciate that optimum feed-through effects can be achieved by making adjustments within these ranges.

Various surfactants such as those described above are suitable for use in the formulations of the present invention. Non-limiting examples of additional surfactants include non-ionic surfactants such as polysorbate and polyethoxylated castor oil, ionic surfactants derived from a lecithin, and surfactants derived from a methyl glucoside coconut oil ester. In certain instances, the ratio of pesticide to surfactant is from about 1:1000 to about 1:1 w/w, e.g., from about 1:500 to about 1:100 w/w, from about 1:100 to about 1:50 w/w, from about 1:50 to about 1:25 w/w, from about 1:25 to about 1:10 w/w, or from about 1:10 to about 1:1 w/w. In certain other instances, the ratio of pesticide to surfactant is from about 1000:1 to about 1:1 w/w, e.g., from about 500:1 to about 100:1 w/w, from about 100:1 to about 50:1 w/w, from about 50:1 to about 25:1 w/w, from about 25:1 to about 10:1 w/w, or from about 10:1 to about 1:1 w/w. One skilled in the art will appreciate that optimum feed-through effects can be achieved by making adjustments within these ranges.

In other embodiments, the formulations of the present invention further comprise a biopolymer such as a carbohydrate. Suitable carbohydrates include, for example, any of the saccharides described above. Advantageously, the presence of a carbohydrate extends the uniformity of the formulation and affords protection against chemical oxidation and UV degradation.

In certain instances, the amount of lignin-pesticide complex in the solid formulations of the present invention is from about 0.001% w/w to about 90% w/w, e.g., from about 0.001% w/w to about 75% w/w, from about 0.001% w/w to about 50% w/w, from about 0.01% w/w to about 20% w/w, or from about 0.01% w/w to about 10% w/w. In certain other instances, the amount of lignin-pesticide complex in the liquid formulations of the present invention is from about 0.001% w/v to about 90% w/v, e.g., from about 0.001% w/v to about 75% w/v, from about 0.001% w/v to about 50% w/v, from about 0.01% w/v to about 20% w/v, or from about 0.01% w/v to about 10% w/v.

VI. Methods of Making

In certain aspects, the present invention provides a method of making a lignin-pesticide complex. The formation of lignin-pesticide complexes relies on intermolecular interactions between the pesticide and lignin. Such interactions include, without limitation, covalent, cross-linking, hydrogen bonding, ionic, van der Waals forces, and dipole-dipole interactions. In a preferred embodiment, the lignin is associated with the pesticide through hydrogen bonding or van der Waals forces. Suitable manufacturing processes for producing complexes of lignin and one or more pesticides include, without limitation, a simple blending method, a solvent method, a solvent co-precipitation or solvent forcing-out method, a vapor method, and a cooking method. These methods are described below.

1. Simple blending method: A pesticide (e.g., methoprene) is sprayed onto lignin (e.g., in fine powder) in a mixer and the resulting mixture is allowed to age for about one to two years at room temperature. Lignin-pesticide complex formation can be accelerated if the mixture is stored under elevated temperature (e.g., about 40° C. to 50° C.).
2. Solvent method: A pesticide (e.g., methoprene, tetrachlorvinphos, cyromazine) is dissolved in an organic solvent such as an alcohol (e.g., methanol, ethanol, isopropanol), ketone (e.g., acetone, methylethylketone), ester (e.g., methyl acetate, ethyl acetate, amyl acetate), acetonitrile, aromatic or aliphatic hydrocarbon, etc. The solution is then sprayed onto lignin (e.g., in fine powder) in a mixer. Finally, the solvent is vaporized to obtain the lignin-pesticide complex.
3. Solvent co-precipitation or solvent forcing-out method: A pesticide (e.g., methoprene) is dissolved in a water-miscible organic solvent (e.g., methanol, ethanol, acetone, isopropanol) or made into an oil in water emulsion of microemulsion. While stirring, lignin is dispersed in water to form a lignin suspension. Next, the pesticide/organic solution or emulsion/microemulsion is added drop-wise to the lignin suspension; in case of emulsion/microemulsion, chemical agent that will destroy the emulsion/microemulsion system (such as electrolytes, e.g., sodium chloride, etc.) is also added to the suspension. A clear supernatant without an oily film floating on top of the water indicates that the pesticide has been deposited onto the fine lignin particles. Filtration and drying steps are then employed to obtain the lignin-pesticide complex as a powder. In the absence of lignin or lignin-pesticide complex formation, the pesticide would be separated from the lignin as an oily layer or oil droplets on top of the water.
4. Solvent co-precipitation or solvent forcing-out method: A pesticide (e.g., methoprene) is dissolved in a water-miscible alcohol (e.g., methanol, ethanol, isopropanol). While stirring, lignin is dispersed in water to form a lignin suspension. Next, the pesticide/alcohol solution is added drop-wise to the lignin suspension. A clear supernatant without an oily film floating on top of the water indicates that the pesticide has been deposited onto the fine lignin particles. Filtration and drying steps are then employed to obtain the lignin-pesticide complex as a powder. In the absence of lignin or lignin-pesticide complex formation, the pesticide would be separated from the lignin as an oily layer or oil droplets on top of the water.
5. Vapor method: A pesticide (e.g., methoprene) is vaporized under vacuum and heat. The resulting vapor is then introduced into a sealed vessel filled with powdered lignin. Agitation or rotation of the vessel assures the uniformity of the lignin-pesticide complex.
6. Cooking method: A pesticide (e.g., methoprene, atomized if possible) is sprayed onto lignin. The mixture is then placed into a sealed vessel under nitrogen or vacuum and heated to an elevated temperature (e.g., about 200° C. to 300° C.) for about 30 minutes to obtain the lignin-pesticide complex. The nitrogen or vacuum environment eliminates the oxidative degradation of pesticides such as methoprene.
7. Supercritical fluid method. A method for making a lignin-pesticide complex, comprising: admixing a pesticide (e.g., methoprene) with a super critical fluid (e.g., carbon dioxide) with powdered lignin in a vessel to form a lignin-pesticide mixture; and releasing the super critical fluid as a gas to make the lignin-pesticide complex.

VII. Uses

In certain aspects, the present invention provides a method for controlling or treating an insect on an animal such as livestock (e.g., cattle, sheep, swine, goats, poultry, horses, and fur-bearing animals) or pets (e.g., cats, dogs, rabbits, horses, birds, and rodents). The method includes administering a lignin-pesticide complex as a feed-through product to the animal, wherein the complex is formulated into a final form such as a granule, a particle, a pellet, a capsule, a microcapsule, a cube, a tablet, a microtablet, a complete feed ration, a liquid feed ration, or any of the final forms described above. The feed-through product is allowed to pass through the animal into its manure. The pesticide is released in the manure, thereby controlling the insect. Without being bound to any particular theory, it is believed that the bioavailability in the manure is due to the effect of fungi on the lignin. As lignin is not susceptible to the organisms and enzymes in the ruminant gut, it is susceptible to fungi prevalent in soil.

In one example, cattle are unacceptably infested with horn flies. Adult horn flies live 2 to 4 weeks piercing the hide and sucking 20 to 30 blood meals a day from the cattle. The lignin-pesticide complex formulated as a feed-through product is ingested with the cattle's feed. As they graze, cattle disperse the pesticide via their manure. The present invention breaks the life cycle of the horn fly by, for example, preventing pupae from molting into adults. In 1 to 2 days, eggs laid in the pesticide-treated manure hatch into larvae. After 3 to 5 days, the larvae molt into pupae. Preferably, the present invention prevents adult emergence following pupal stage and therefore breaks the horn fly cycle.

VIII. Examples

The following examples are offered to illustrate, but not to limit, the claimed invention.

Example 1

Determination of Maximum Amount of Active Agent to Pass into the Manure of Chickens This example illustrates a determination of the maximum concentration of any active agent that will pass into the manure of chickens.

Briefly, chicken feed was formulated using a pulverized cattle bolus which contained barium in the form of $BaSO_4$. Table 1 shows the amount of barium expressed as a percentage in the feed or in the manure at 4, 24, 48, and 72 hours after feeding.

TABLE 1

Amount of barium found in the feed and in the manure of chickens.

| | Amount of Barium | | | | |
|---|---|---|---|---|---|
| | % in | % found in manure at given times | | | |
| Formulation | Feed | 4 hr. | 24 hr. | 48 hr. | 72 hr. |
| Barium (as $BaSO_4$) from 491-101 w/bolus | 0.093% | 0.00165% | 0.0455% | 0.0557% | 0.0471% |
| % of initial $BaSO_4$ | 100% | 1.78% | 48.90% | 59.90% | 50.60% |

This study shows that the maximum concentration of any active agent (e.g., pesticide) that will pass into the manure of a chicken is about 50% of the applied dose in the feed. Without being bound to any particular theory, it is thought that dilution of the active agent with water causes this effect. For example, if the feed is dosed at 20 parts per million (ppm), a typical feed-through product yields a maximum of 10 ppm of active agent in the wet manure.

Example 2

Characterization of Lignin-Methoprene Formulations in Chickens

This example illustrates a study in chickens comparing several inventive formulations containing lignin-methoprene complexes with various control formulations.

Briefly, chicken feed was formulated with the inventive lignin-methoprene complexes described herein. Formulations containing lignin and charcoal, lignin complexes, lignin-mineral wax complexes, or free methoprene and lignin were used as controls. Table 2 shows several advantageous characteristics of the lignin-methoprene formulations of the present invention. For example, a substantially greater amount of methoprene was recovered from the manure of chickens that were fed formulations containing lignin-methoprene complexes (31.1-53.1%) than in the manure of chickens that were fed control formulations (9.4-20.0%). In addition, chickens that were fed formulations containing lignin-methoprene complexes produced manure that virtually eliminated the emergence of flies (86.29-100%) as compared to chickens that were fed control formulations (27.51-71.14%).

TABLE 2

Characteristics of the lignin-methoprene formulations of the present invention.

| Formulation | Feed rate (ppm) | Manure (ppm) | % of Feed | % Control |
|---|---|---|---|---|
| Charcoal premix coated with Lignin | 34.1 | 3.2 | 9.4 | 71.14 |
| Free methoprene mixed with lignin, not aged | 29.5 | 5.9 | 20.0 | 36.84 |
| Lignin-mineral wax complex | 34.2 | 4.6 | 13.5 | 52.79 |
| Free methoprene mixed with lignin, not aged | 20.9 | 3.3 | 15.8 | 27.51 |
| Lignin-methoprene complex | 35.1 | 12.3 | 35 | 98.35 |
| Lignin-methoprene complex | 42.9 | 14.6 | 34.0 | 86.29 |
| Lignin-methoprene complex | 35.1 | 17.4 | 50 | 99.26 |
| Lignin-methoprene complex | 42.9 | 19.1 | 45.0 | 97.92 |
| Lignin-methoprene complex | 35.1 | 10.9 | 31.1 | 100 |
| Lignin-methoprene complex | 33.7 | 17.9 | 53.1 | 99.23 |
| Lignin-methoprene complex (scale up) | 33.7 | 15.4 | 45.7 | 100 |
| Lignin-methoprene complex (scale up) | 33.7 | 14.85 | 44.1 | 98.61 |

Feed rate (ppm): The amount of methoprene, in parts per million, that was fed to the chickens.
Manure (ppm): The amount of methoprene, in parts per million, that was found in the manure after consuming treated feed for 24 hours.
% of Feed: A comparison of the amount of methoprene recovered in the manure vs. the amount of methoprene that was fed, as a percentage.
% Control: A comparison of the number of flies that emerge from the treated vs. the non-treated manure, expressed as a percentage.

Example 3

Characterization of Lignin-Methoprene Formulations in Cats

This example illustrates a study in cats comparing an inventive formulation containing lignin-methoprene complexes with a formulation containing free methoprene.

Briefly, cats were fed two formulations of treated food to determine if the lignin-methoprene complex improved the pass through effect of methoprene as compared to free methoprene. Three cats were fed the formulations for a week and their manure was tested every 24 hours. Table 3 shows the amount of methoprene recovered from each cat for the two formulations.

TABLE 3

Amount of methoprene found in the manure of cats fed either a free methoprene or a lignin-methoprene formulation.

| Hour | Sample name | Cat food treated with Free Methoprene Lot # 491-166 @ 36.2 ppm Calculated Methoprene (ppm)* | Cat food treated with Lignin-Methoprene Complex Lot # 491-165 @ 40.7 ppm Calculated Methoprene (ppm)* |
|---|---|---|---|
| Day 0 (0 hr) | Q | 0 | 0 |
| | S | 0 | 0 |
| | T | 0 | 0 |

TABLE 3-continued

Amount of methoprene found in the manure of cats fed either a free methoprene or a lignin-methoprene formulation.

| Hour | Sample name | Cat food treated with Free Methoprene Lot # 491-166 @ 36.2 ppm Calculated Methoprene (ppm)* | Cat food treated with Lignin-Methoprene Complex Lot # 491-165 @ 40.7 ppm Calculated Methoprene (ppm)* |
|---|---|---|---|
| Day 1 (24 hr) | Q | 0.6 | Day 1 | 39.3 | Day 1 |
| | S | 0.7 | Avg. | 33.7 | Avg. |
| | T | 0.6 | 0.63 ppm (1.7%) | 43.2 | 38.7 ppm (95.1%) |
| Day 2 (48 hr) | Q | 2.4 | Day 2 | n/a | Day 2 |
| | S | 2.5 | Avg. | 59.9 | Avg. |
| | T | 1.6 | 2.2 ppm (6.1%) | 68.1 | 64.0 ppm (157.2%) |
| Day 3 (72 hr) | Q | 2.0 | Day 3 | 135.6 | Day 3 |
| | S | 2.0 | Avg. | 66.0 | Avg. |
| | T | 1.5 | 1.8 ppm (5.0%) | 56.2 | 85.0 ppm (208.8%) |
| Day 4 (96 hr) | Q | 2.8 | Day 4 | 104.7 | Day 4 |
| | S | 1.7 | Avg. | 84.0 | Avg. |
| | T | 1.3 | 1.9 ppm (5.2%) | 65.9 | 84.9 ppm (208.5%) |

This study shows that a substantially greater amount of methoprene was recovered from the manure of cats that were fed a formulation containing lignin-methoprene complexes (95.1-208.8%) than in the manure of cats that were fed a formulation containing free methoprene (1.7-6.1%).

Example 4

Spectrometric Analysis of Lignin-Methoprene Formulations

This example illustrates a study of the inventive formulation containing lignin-methoprene complexes using Fourier Transform Infrared (FTIR) spectroscopy.

Figure 2:
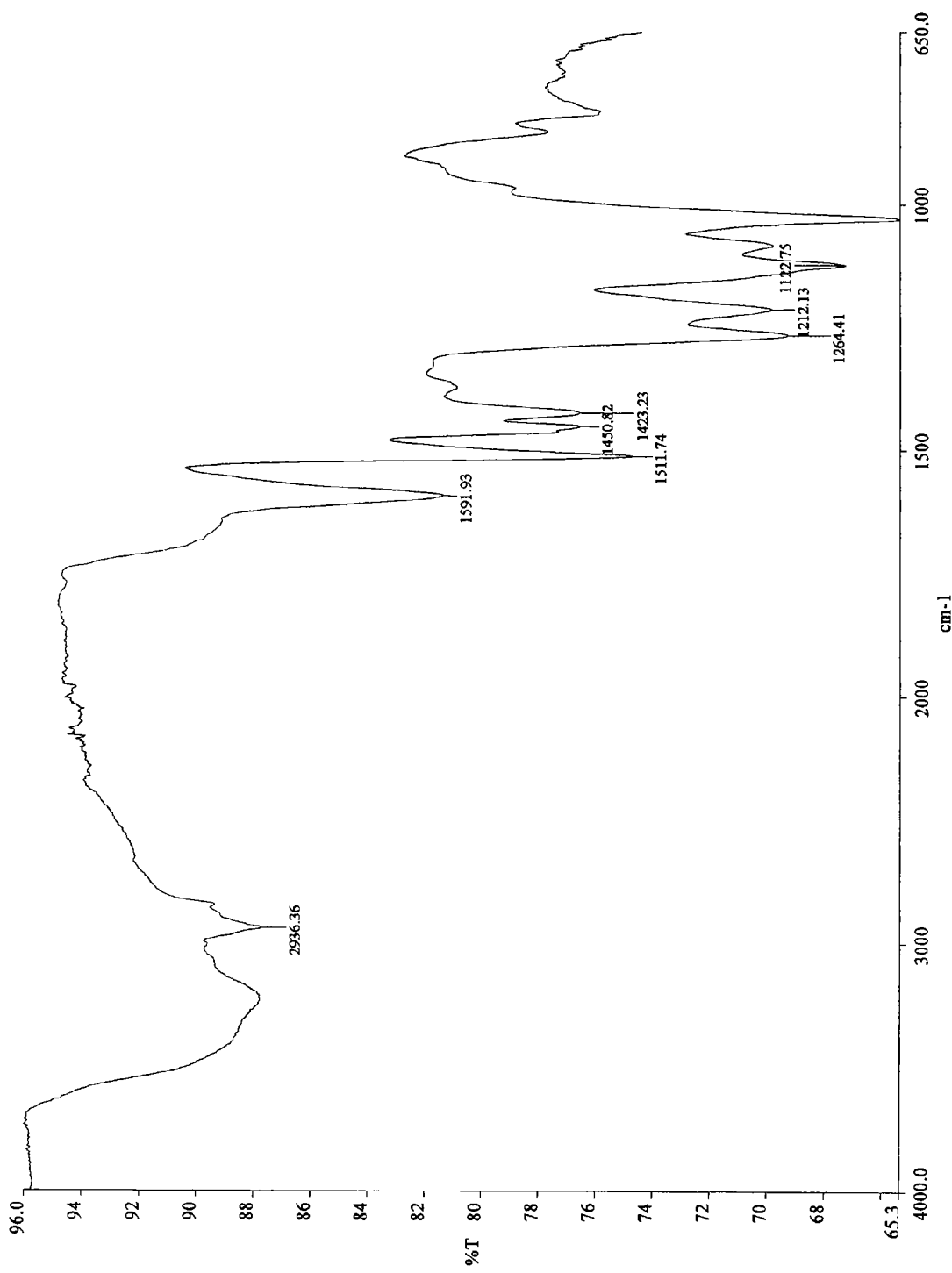
FIG. 2 shows the FTIR spectrum of lignin raw material.
Figure 3:
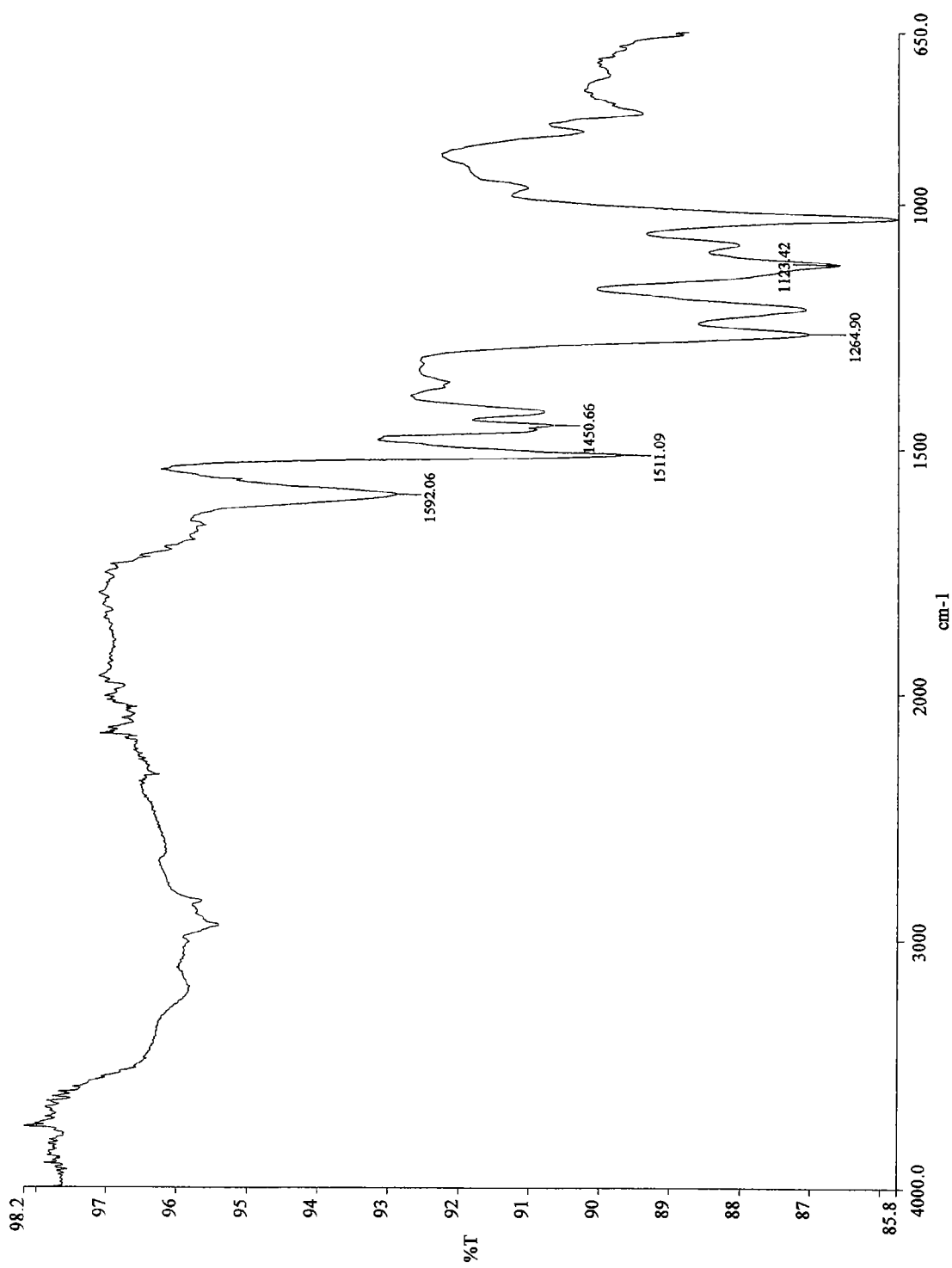
FIG. 3 shows the FTIR spectrum of ground lignin raw material.

As shown in FIG. 1, methoprene exhibited a C=O absorbance at 1707-1708 cm$^{-1}$ (1707.21). FIG. 2 shows that lignin raw material did not have any absorbance in the 1700 cm$^{-1}$ region. Similarly, FIG. 3 shows that ground lignin raw material did not have any absorbance in the 1700 cm$^{-1}$ region.

Figure 4:
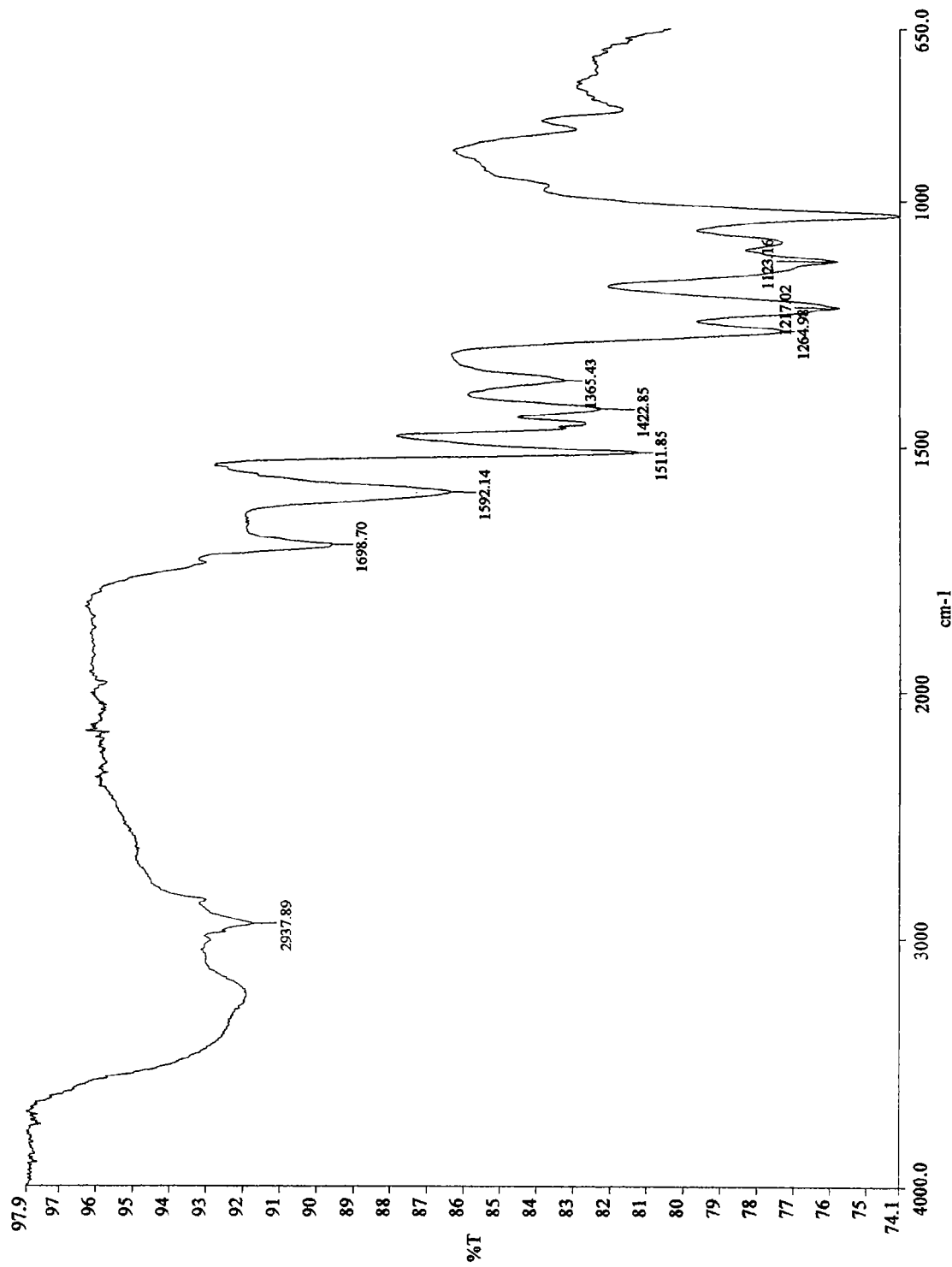
FIG. 4 shows the FTIR spectrum of a formulation containing lignin and 1% methoprene.
Figure 5:
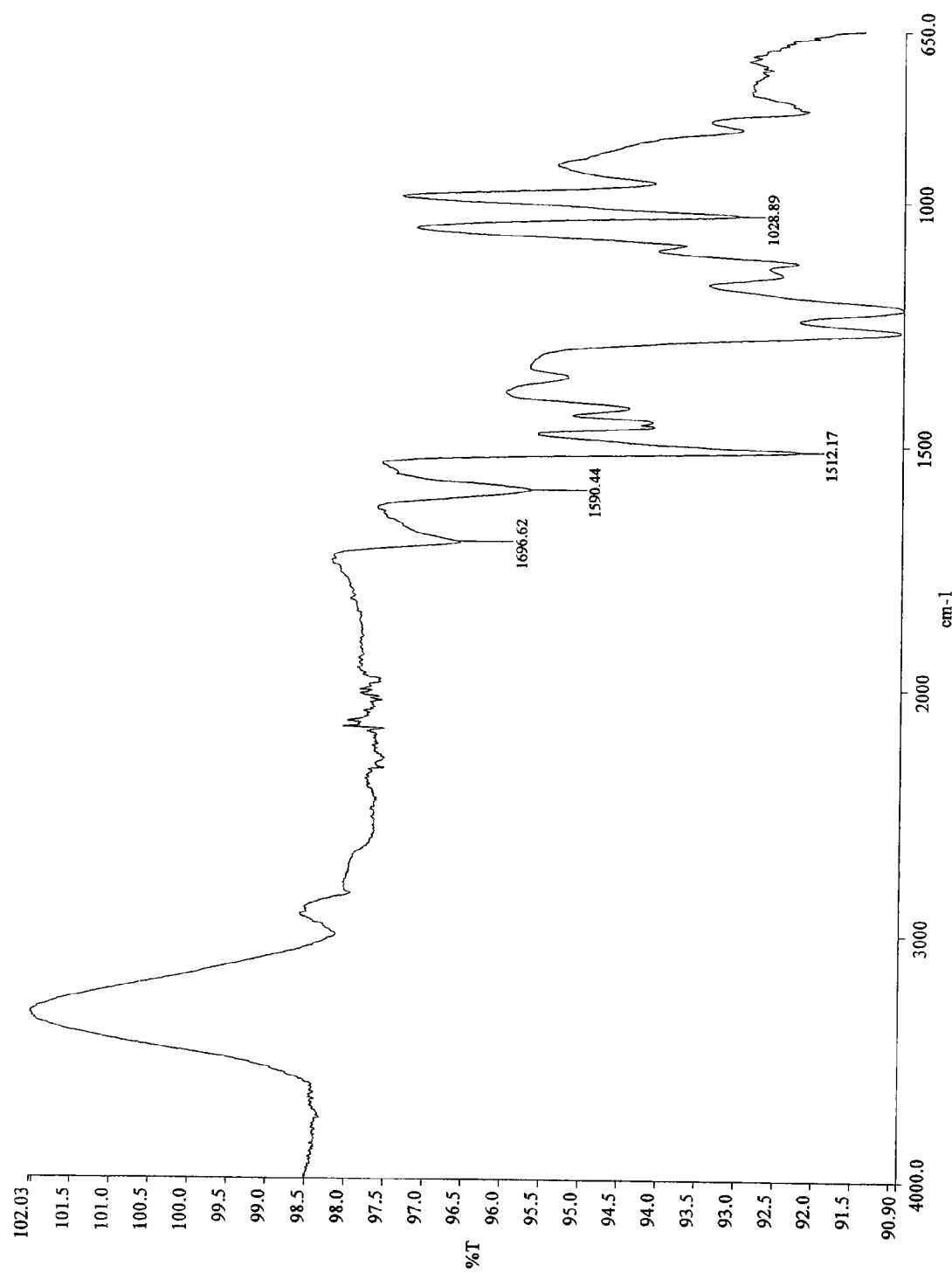
FIG. 5 shows the FTIR spectrum of a formulation containing ground lignin and 1% methoprene.
Figure 6:
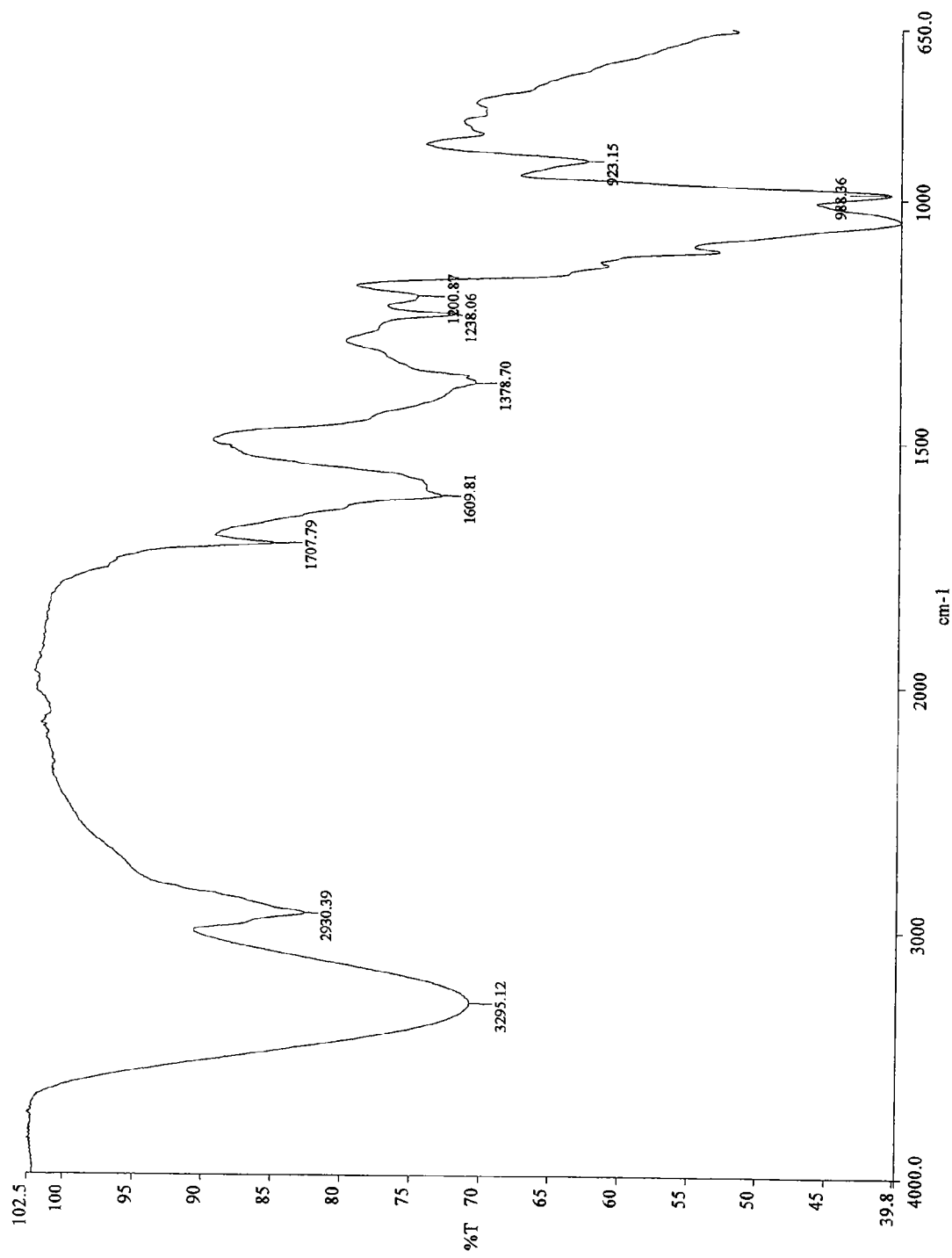
FIG. 6 shows the FTIR spectrum of CP-2, a control 2% methoprene formulation that does not contain lignin.

In contrast, FIG. 4 shows that a formulation containing lignin and 1% methoprene exhibited a shift of the C=O absorbance from 1707-1708 cm$^{-1}$ to 1698-1699 cm$^{-1}$ (1698.70). This shift in C=O absorbance is attributed to the formation of a hydrogen bond between methoprene and lignin (see, e.g., Silverstein et al., In Spectrometric Identification of Organic Compounds, 5th Ed., John Wiley & Sons, Inc., pp. 95-96). Similarly, FIG. 5 shows that a formulation containing ground lignin and 1% methoprene exhibited a shift of the C=O absorbance from 1707-1708 cm$^{-1}$ to 1696-1697 cm$^{-1}$ (1696.62). The 2% methoprene cattle product CP-2, which does not contain lignin, was used as a control. As shown in FIG. 6, this control formulation also did not exhibit a shift of the C=O absorbance from 1707-1708 cm$^{-1}$.

Without being bound to any particular theory, it is believed that in certain instances, in order to form a lignin-pesticide complex, the pesticide preferably possesses a planar region in its molecular structure. For example, with respect to metho prene, the planar region comprises the ester moiety and its conjugated diene functionality as shown below.

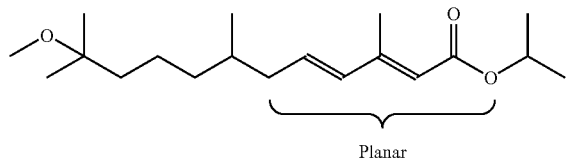

Planar

It is believed that this planar region "stacks" with the planar phenyl rings of a lignin polymer and additionally hydrogen-bonding occurs between the oxygen of the carbonyl ester of methoprene and the hydroxyl on the phenyl ring of the lignin polymer. Further, it is believed that the aromatic rings in lignin can form a complex-like (e.g., intermolecular interaction) structure with the two conjugated double bonds of methoprene when especially "closely stacked."

The above experiments demonstrate the surprising discovery that lignin and methoprene are associated as a complex through hydrogen bonding. Due to this intermolecular interaction between lignin and methoprene, lignin-methoprene complexes are suitable as feed-through animal products by advantageously protecting methoprene against intestinal absorption and enzyme and microbial digestion in an animal and allowing methoprene to pass through the animal into its manure, where it is released for effective pest control. Although methoprene is described in this example, one skilled in the art will appreciate that lignin can be associated with other pesticides through similar hydrogen bonding interactions or through other intermolecular forces such as van der Waals forces.

Example 5

Comparison Example of Enteric coated-Methoprene Formulations

This example illustrates a study of methoprene versus enteric coated methoprene. The results below indicate that there is no difference in % recovery between technical grade methoprene and enteric coated methoprene or matrix treated methoprene.

TABLE 4

Amount of methoprene found in the manure of chickens fed a technical grade methoprene, enteric coated methoprene, and matrix treated methoprene.
Enteric Matrix/Coating of Methoprene Feed Through Study

| Substance | Feed Rate ppm | Manure Rate ppm | % Recovery |
|---|---|---|---|
| Methoprene technical | 23.8 | 2.91 | 12.22 |
| Eudragit ® Matrix | 23.9 | 2.79 | 11.67 |
| Eudragit ® Coating | 25.1 | 2.61 | 10.39 |

Chicken Feed Used: Egg Buster
Polymer Used: Eudragit ® LS100 for coating Polymethylacrylate commercially available from Degusa Co.

These data indicate that enteric coating with Eudragit will not protect methoprene from gastrointestinal absorption or degradation.

Example 6

Characterization of Lignin-Methoprene Formulations in Horses

This example illustrates a study in horses comparing an inventive formulation containing a lignin-methoprene complex with a formulation containing free methoprene.

Briefly, horses were fed two formulations of treated feed as a top dressing to determine the efficiency of a lignin-methoprene complex improved the pass through effect of methoprene as compared to free methoprene. Four horses were fed the formulations for eleven days and their manure was tested every 24 hours. Table 5 shows the average amount of methoprene recovered from each horse for the two formulations.

TABLE 5

Amount of methoprene found in the manure of horses fed either a free methoprene or a lignin-methoprene formulation.

| | | Average of Day 0-Day 10 | | | |
|---|---|---|---|---|---|
| | Animal ID | AI fed (ppm) | AI manure (ppm) | Percent pass through | Avg. % pass through by Group |
| Group 1 | Drambouie | 10.19 | 3.59 | 35.2 | 34.95 |
| (inventive) | Maggie | 12.43 | 4.31 | 34.7 | |
| Group 2 | Bettor Lad | 8.94 | 1.29 | 14.4 | 14.75 |
| (comparative) | Dancer | 8.61 | 1.30 | 15.1 | |

AI fed (ppm): The amount of methoprene, in parts per million, that was fed to the horses.
AI manure (ppm): The amount of methoprene, in parts per million, that was found in the manure after consuming treated feed for 24 hours.
% pass through: A comparison of the amount of methoprene recovered in the manure vs. the amount of methoprene that was fed, as a percentage.

This study shows that a greater amount of methoprene (>than 2x) was recovered from the manure of horses that were fed a formulation containing a lignin-methoprene complex (34.95% pass through) than in the manure of horses that were fed a formulation containing free methoprene (14.75% pass through).

Example 7

Characterization of Lignin-Methoprene Formulations in Cattle

This example illustrates a study in cattle comparing an inventive formulation containing a lignin-methoprene complex with a formulation containing free methoprene.

Briefly, cows were fed two formulations of treated feed as a top dressing to determine if the lignin-methoprene complex improved the pass through effect of methoprene as compared to free methoprene. Four cows were fed the formulations for eleven days and their manure was tested every 24 hours. Table 6 shows the amount of methoprene recovered from each cow for the two formulations.

TABLE 6

Amount of methoprene found in the manure of cows fed either a free methoprene or a lignin-methoprene formulation.

| | Animal ID | AI fed ppm | Average of Day 1-Day 10 AI manure ppm | Percent pass through | Avg. % pass through by Group |
|---|---|---|---|---|---|
| Group 1 (inventive) | 44 R/W | 8.14 | 2.24 | 27.5 | 24.65 |
| | 44 Black | 9.26 | 2.02 | 21.8 | |
| Group 2 (Comparative) | 10 R/W | 8.94 | 0.16 | 1.8 | 2.3 |
| | 16 Black | 12.58 | 0.35 | 2.8 | |

AI fed (ppm): The amount of methoprene, in parts per million, that was fed to the cows.
AI manure (ppm): The amount of methoprene, in parts per million, that was found in the manure after consuming treated feed for 24 hours.
% pass through: A comparison of the amount of methoprene recovered in the manure vs. the amount of methoprene that was fed, as a percentage.

This study shows that a substantially greater amount of methoprene (over 10×) was recovered from the manure of cows that were fed a formulation containing lignin-methoprene complexes (24.65% pass through) than in the manure of cows that were fed a formulation containing free methoprene (2.3% pass through).

Example 8

Method of Making a Lignin-Methoprene Complex Using Super Critical Fluid as a Solvent This example illustrates a method of making a lignin-methoprene complex using super critical fluid as a solvent.

Figure 7:
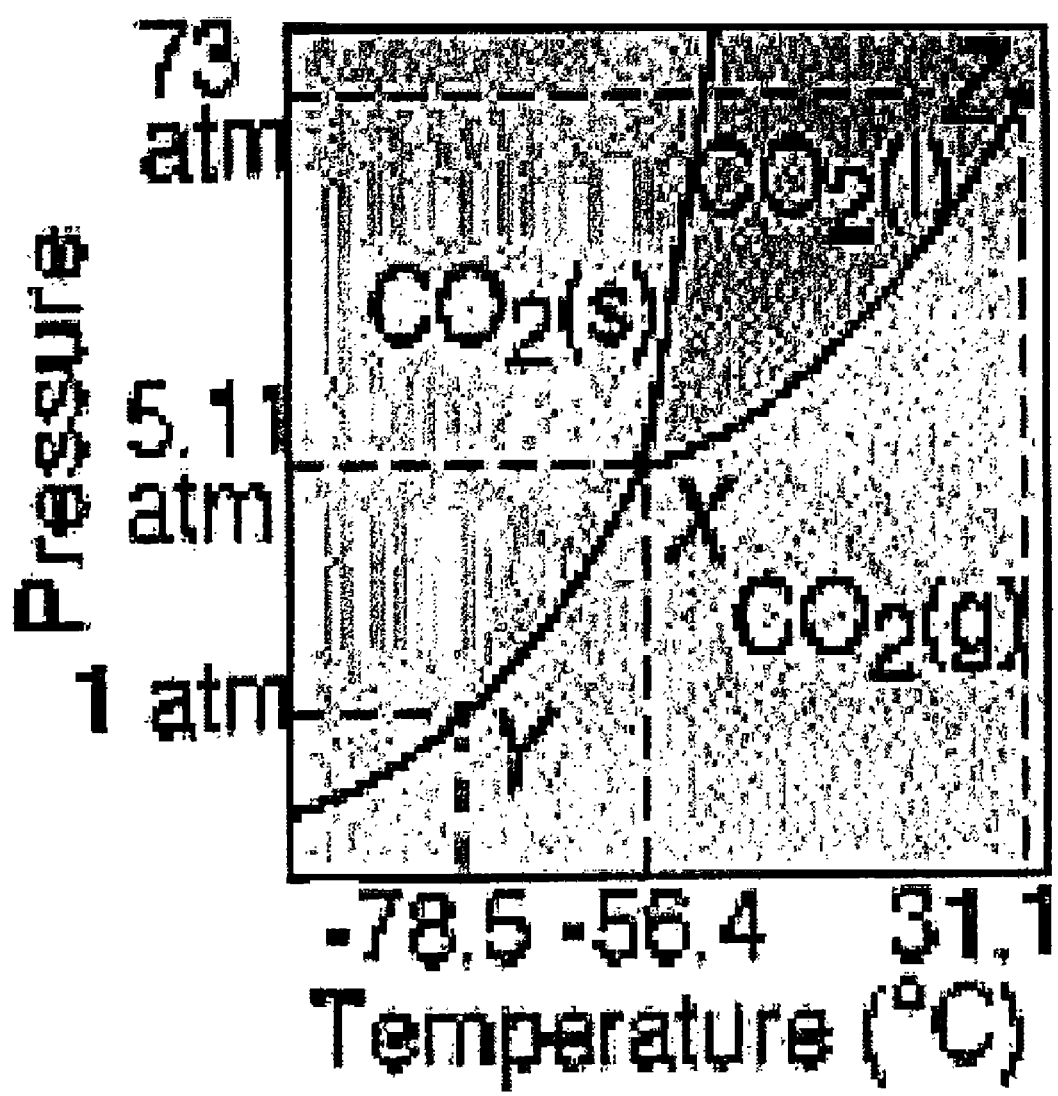
FIG. 7 shows a phase diagram useful in the present invention.

In one aspect, the complexes of the present invention can be made using a super critical fluid, such as carbon dioxide, as a solvent. Since methoprene is susceptible to oxidation, it is possible to blanket liquid in a container with an inert gas such as nitrogen, or carbon dioxide gas, to prevent oxidation. Surprisingly, it has been found that methoprene is able to absorbed large volumes of carbon dioxide. Advantageously, a methoprene/lignin complex can be made using a supercritical fluid such as carbon dioxide ($scCO_2$) as solvent. As the triple point (see FIG. 7) of carbon dioxide is around 5.11 atm at −56.4° C., it is convenient to use a high pressure pump to achieve a pressure of 71-72 Bar (one Bar unit is equal to 0.98697 Atm (Atmospheric Pressure) or 105 Newton per square meter and 34° (31-35°). The temperature and the pressure will affect the solubility of the materials (i.e., methoprene and lignin) in the $scCO_2$. The location of the triple point of a pure substance occurs at a single definite pressure and temperature characteristic of that substance. For water, the triple point is at 273.16 K and 611 Pa or 4.58 Torr, and the three phases of water co-exist in equilibrium at no other combination of pressure and temperature. The triple point marks the lowest pressure at which a liquid phase of a substance can exist.

Method of Making

Methoprene is added to a $scCO_2$ vessel and the fluid is then introduced into a pressurized cell with powdered lignin. The mixture in the cell is mixed and the pressure is then released by pumping the gaseous $CO_2$ out of the cell, the gas is recovered for reuse. Both methoprene and lignin are placed in the cell and the $CO_2$ is introduced into the cell. The mixture in the cell is mixed and the $CO_2$ gas is then recover for reuse.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A lignin-pesticide complex free of non-hydrogen bonded pesticide, said complex formulated as a feed-through product comprising:
    a lignin, wherein said lignin is an alkali lignin;
    a pesticide, wherein said pesticide is methoprene and wherein said lignin and said pesticide are associated as a non-covalent bonded complex through hydrogen bonding and the amount of pesticide in the complex is about 0.01% w/w to about 2% w/w, wherein said lignin-pesticide complex is substantially free of non-associated pesticide; and
    wherein said lignin-pesticide complex is free of non-hydrogen bonded pesticide and is formulated as a feed-through product.

2. The complex of claim 1, wherein said alkali lignin is selected from the group consisting of a Kraft lignin, a sodium salt of lignin, a potassium salt of lignin, a soda lignin, an ammonium salt of lignin, an amine salt and combinations thereof.

3. The complex of claim 1, wherein the amount of pesticide in the complex is about 1% w/w to about 2% w/w.

4. The complex of claim 3, wherein the amount of pesticide in the complex is about 2% w/w.

5. The complex of claim 1, wherein said alkali lignin is Kraft lignin.

6. A feed-through formulation for controlling a manure breeding insect on an animal, wherein the feed-through formulation is free of non-hydrogen bonded pesticide, said formulation comprising:
    an alkali lignin; and
    an insect growth regulator (IGR) pesticide selected from the group consisting of methoprene and diflubenzuron, wherein said alkali lignin and IGR pesticide are associated as a non-covalent bonded complex through hydrogen bonding and the amount of pesticide in the complex is about 0.01% w/w to about 2% w/w, wherein said feed-through formulation passes through said animal into an excrement, wherein said lignin-pesticide complex is free of non-hydrogen bonded pesticide and is formulated as a feed-through formulation.

7. The feed-through formulation of claim 6, wherein the amount of IGR pesticide in the complex is about 1% w/w to about 2% w/w.

8. The feed-through formulation of claim 7, wherein the amount of IGR pesticide in the complex is about 2%.

9. The feed-through formulation of claim 6, wherein said alkali lignin is Kraft lignin.

10. The feed-through formulation of claim 6, wherein said IGR pesticide is diflubenzuron.

11. The feed-through formulation of claim 6, wherein said IGR pesticide is methoprene.

12. A method for controlling a manure breeding insect on an animal, said method comprising:
    administering a lignin-pesticide complex as a feed-through product to said animal, wherein said pesticide is methoprene and said lignin-pesticide is complexed by non-covalent hydrogen bonding and the amount of pesticide in the complex is about 0.01% w/w to about 2% w/w, wherein said lignin-pesticide complex is substantially free of non-associated pesticide and free of non-hydrogen bonded pesticide; and allowing said feed-through product to pass through said animal intact into an excrement, wherein the pesticide is subsequently bioavailable in the manure, thereby controlling said manure breeding insect.

13. The method of claim 12, wherein said animal is livestock.

14. The method of claim 13, wherein said livestock is selected from the group consisting of cattle, sheep, swine, goats, poultry, horses, and fur-bearing animals.

15. The method of claim 14, wherein said fur-bearing animal is selected from the group consisting of rabbits, foxes, minks, chinchillas, beavers, muskrats, martens, otters, ferrets, nutrias, and bears.

16. The method of claim 14, wherein said livestock is cattle.

17. The method of claim 14, wherein said livestock is swine.

18. The method of claim 14, wherein said livestock is horses.

19. The method of claim 12, wherein said animal is a pet.

20. The method of claim 19, wherein said pet is selected from the group consisting of cats, dogs, rabbits, horses, birds, reptiles and rodents.

* * * * *